US012577596B2

(12) United States Patent
García Gil De Muñoz

(10) Patent No.: US 12,577,596 B2
(45) Date of Patent: Mar. 17, 2026

(54) METHOD FOR OBTAINING CARMINIC ACID

(71) Applicant: CARINLAB S.A.P.I. DE C.V., Tlalnepantla de Baz (MX)

(72) Inventor: Fernando Luis García Gil De Muñoz, Naucalpan de Juárez (MX)

(73) Assignee: CARINLAB S.A.P.I. DE C.V., Tlalnepantla de Baz (MX)

(*) Notice: Subject to any disclaimer, the term of this patent is extended or adjusted under 35 U.S.C. 154(b) by 484 days.

(21) Appl. No.: 18/005,642

(22) PCT Filed: Jun. 28, 2021

(86) PCT No.: PCT/IB2021/055774
§ 371 (c)(1),
(2) Date: Jan. 16, 2023

(87) PCT Pub. No.: WO2022/013659
PCT Pub. Date: Jan. 20, 2022

(65) Prior Publication Data

US 2023/0287467 A1 Sep. 14, 2023

(30) Foreign Application Priority Data

Jul. 16, 2020 (MX) .................... MX/a/2020/007632

(51) Int. Cl.
*C12P 17/06* (2006.01)
*A23L 5/43* (2016.01)
*C07D 309/10* (2006.01)
*C12N 5/07* (2010.01)

(52) U.S. Cl.
CPC ................. *C12P 17/06* (2013.01); *A23L 5/43* (2016.08); *C07D 309/10* (2013.01); *C12N 5/0601* (2013.01)

(58) Field of Classification Search
CPC .......... C12N 5/0601; C09B 61/00; A23L 2/58
See application file for complete search history.

(56) References Cited

U.S. PATENT DOCUMENTS 8,919,281 B2 12/2014 Hendrickson et al.

FOREIGN PATENT DOCUMENTS

MX 295682 B 2/2012

OTHER PUBLICATIONS

International Search Report issued in PCT/IB2021/055774 mailed Oct. 20, 2021.

Cortes, D. "Relationship of the Female Reproductive System of Dactyloplus coccus Costa (Hemiptera: Dactilopididea) in the Synthesis of Carminic Acid", 2004, Professional Thesis to Obtain the Title of Bachelor's Degree in Biology and Agriculture, University of Guadalajara, Mexico.

Caselin, S. et al., "Morphological Characterization of Hemocytes in the Female of Dactylopius coccus Costa (Hemiptera: Coccoidea: Dactylopiidea)", Agrociencia, vol. 42, No. 3. Apr.-May 2008 pp. 349-355. Postgraduate College Texcoco, Mexico.

Gonzalez M. et al., In vitro Culture of Embryonic Cells of Mealy Spoil (Dactylopius coccus Costa) at Different pH's, Scientific Note Rev. Fitotec. Mex. vol. 25(2) pp. 209-212, 2002.

*Primary Examiner* — Valarie E Bertoglio
(74) *Attorney, Agent, or Firm* — Heslin Rothenberg Farley & Mesiti P.C.

(57) ABSTRACT

A novel, alternative, low-cost synthesis process for the in vitro production of carminic acid by using the hemolymph cells of the insect *Dactylopius coccus* Costa (cochineal scale insect) for use in the dye industry for food, cosmetics, pharmaceuticals and textiles.

13 Claims, 10 Drawing Sheets

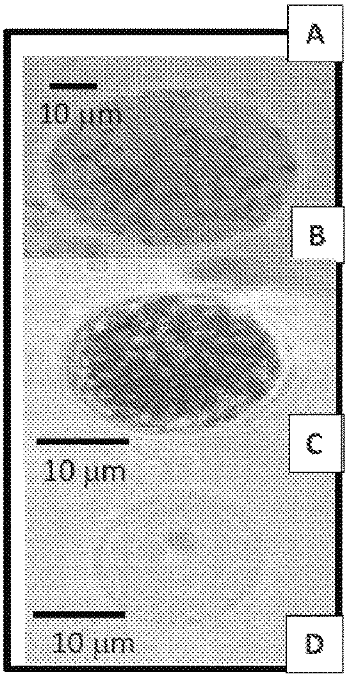
FIG. 1
FIG. 2
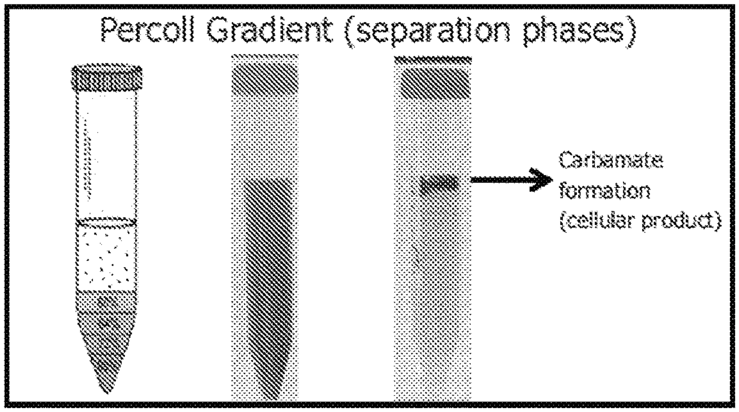

Gr= Granulocytes
Phase contrast microscopy

Results graph:

Std 95% carmine sample
Carmine batch 1 sample
Carmine batch 2 sample

Results graph:

Granulocyte in culture
Day 8

Granulocyte in culture
Day 10

Pattern of soluble
LH proteins in the insect

Technique: PAGE -SDS 10%
Protein concentration=3.8 µg/µl of Hemol

| HL in the melanization process | Inhibition of melanization in HL |

METHOD FOR OBTAINING CARMINIC ACID

CROSS REFERENCE TO RELATED APPLICATIONS

This application is a U.S. National Phase filing under 35 U.S.C. § 371 of International Application PCT/IB2021/055774, filed Jun. 28, 2021, and published as WO 2022/013659 A1 on Jan. 20, 2022, PCT/IB2021/055774 claims priority from Mexican patent application number MX/a/2020/007632, filed Jul. 16, 2020. The entire contents of each of these prior applications are hereby incorporated herein by reference.

FIELD OF THE INVENTION

The present invention relates to a novel, alternative, low-cost process for the in vitro production of carminic acid (CA) for use in the dye industry, with wide applications in the food, cosmetic, pharmaceutical and textile industries, among others.

BACKGROUND OF THE INVENTION

For many years, there have been in the prior art traditional production methods that involve the sowing, growth and harvesting of the *Dactylopius coccus* Costa cochineal scale insects in cycles of approximately 80-90 days using greenhouses, sheds and/or open sky systems. This production requires the pairing of both plants and insects. It is known that the carminic acid extracted from the cochineal scale insect is used as a red and/or crimson dye in cosmetics (lipsticks, among others) and as food additive E-120 in the food industry to give a red color to food, although it is increasingly replaced with cheaper synthetic dyes. A widely used substitute is cochineal red A, a diazo dye with number E-124. Carminic acid obtained from local insects has been used in Europe at least since the Iron Age, and remains have been discovered, for example, in Hallstad culture tombs.

The following methods are known in the art, all of which have the same primary phase of preparing the cochineal insect to extract the carminic acid: drying of the raw material, mechanical separation, grinding, extraction of fats and waxes. They differ in the extraction of fats and waxes and in the extraction of the carminic acid, which is the next stage and then its continuation with the precipitation, settling, filtration and drying of the carmine.

Some state-of-the-art solutions for the production of carminic acid in large quantities are disclosed in the following documents:

Miguel González González et al, Scientific Note Rev. Fitotec. Mex. Vol. 25 (2): 209-212, 2002, "In vitro CULTURE OF EMBRYONIC CELLS OF COCHINEAL (*Dactylopius coccus* Costa) AT DIFFERENT pH VALUES", evaluated the determination of an optimum pH at which in vitro cochineal (*Dactylopius coccus* Costa) cell cultures register maximum acid production, where several pH levels (4.5, 5.0, 5.5, 6.0 and 6.5) and centrifugation fractions (0, 2, 5 and 10 min) were evaluated for macerated cells of cochineal embryos established in Schneider's nutrient medium for culturing insect cell lines. The content of carminic acid present in each sample was determined by high performance liquid chromatography. Pigment was extracted from the samples using a 2M HCl solution. The pigment detection limits were from 1.0 mg L-1 to 120.0 mg L-1. No significant effect of pH was observed on carminic acid content or number of cell lines, although an intermediate pH (5.5) tended to give better results. However, the conclusions of said document indicate that "culture media with a pH of 4.5 to 6.5 are suitable for the in vitro culture of cochineal cells, although intermediate pH values tend to be better in carmine content and the number of cell lines. Centrifugation times of 2 and 5 min were the most suitable for establishing *D. coccus* embryo cell lines. Carmine production in secondary cultures was low. Therefore, it was suggested to evaluate other variables of the culture medium, mainly osmotic pressure and constituents of the nutrient medium.

U.S. Pat. No. 8,919,281 (B2), 2013, Means to culture cochineal insects in an artificial medium, Hendrickson, Constance M. Merkle, Denise Lynn, mentions a method for culturing insects of the genus *Dactylopius*, comprising: heating a mixture comprising (a) a cactus additive obtained from a cactus of the genus Opuntia, (b) a polysaccharide and (c) glucose; combining the heated mixture with a three-dimensional matrix; cooling the combined mixture and matrix to form a hardened medium; and inoculating the hardened medium with a species selected from the group consisting of the genus *Dactylopius*.

For its part, MX 295682, ARIGEN PHARMACEUTICALS, INC, LYMPHOKINE-ACTIVATED KILLER CELL PROLIFERATION METHOD, Watarai, Shinobu; Nishikawa, Shigeru, mentions a cancer-associated cell proliferation/activation method that can be performed at such low costs that the methods may be applicable to non-human animals; A cell proliferation/activation method of the present application comprises the steps of, during cell culture, supplementing with at least 5-15 μg/ml of concanavalin A and a growth factor having interleukin-2-like activity to the culture medium and therefore the present method can proliferate/activate αβ cells on a preferential basis.

However, despite the solutions provided there is still a need in the art for solutions that are effective and that allow a reduction in production times and immediate harvests of carminic acid, as well as in operating and human resource costs. The present invention solves this problem by providing a novel and inventive process for the in vitro production of carminic acid of the following structure:

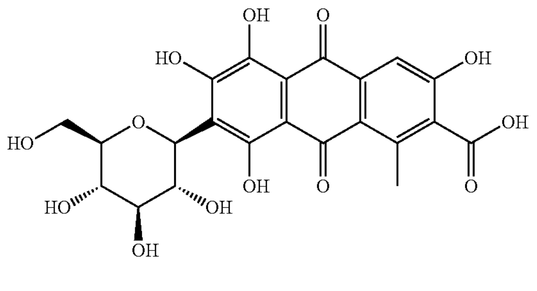 [SMILES: Cc1c(C(=O)O)c(O)cc2c1C(=O)c1c(O)c([C@@H]3O[C@H](CO)[C@@H](O)[C@H](O)[C@H]3O)c(O)c(O)c1C2=O]

BRIEF DESCRIPTION OF THE INVENTION

The present invention relates in particular to a process for the in vitro production of carminic acid, wherein the process is based on the isolation, purification and permanence of a hemocyte cell line obtained from egg-filled adult females of *Dactylopius coccus* Costa cochineal scale insects that are cultured to generate a primary culture (phase I) and subsequently stimulate hemocytes with a mixture of mitogens.

Advantageously, the production of carminic acid through the novel process of the present invention provides a reduction both in the number of insects to be used and in the production and harvest times that are now estimated to be between approximately 12-14 days, as well as a reduction in operating costs and human resources; large quantities are produced in a reduced space and management is with cells in laboratory conditions without the need to handle large volumes of inputs, reduction of raw material (elimination of host plants), harvest in direct soluble form without the need for drying processes (time and materials), cryo-preservation of a production cell line for perpetuity in case insect populations are scarce in the future, pest- and natural predator-free production, use of fewer insects in an amount of approximately 10-15 individuals to produce the same amount compared to traditional methods that require sacrificing approximately 350,000 to approximately 400,000 *Dactylopius coccus* Costa cochineal insects to produce approximately one kilogram of carminic acid; the production cost is approximately 50% less than the costs using traditional methods, in addition to being a scalable process by reproducing production units.

According to the present invention, a methodology is provided to isolate, extract and maintain a pure CA-producing cell line in order to obtain reproducible and constant CA production harvests under laboratory conditions and in 1000 ml container production, as well as to maintain contaminant-free cells lines in a constant way that are reproducible and can be replicated before the stimulus that is administered to the cultures.

DESCRIPTION OF THE FIGURES

The particular features and advantages of the invention, as well as other objects thereof, will become apparent from the following description, taken in relation to the accompanying figures:

FIG. 1 shows Phase I of the extraction of hemocytes from the hemolymph of the *Dactylopius coccus* Costa insect, in which:

A and B are chromatocytes (separated and concentrated in a 70% Percoll® (polyvinylpyrrolidone-coated silica particle) gradient), cultured for 96 hours in Schneider medium. A and B are the same type of cells with different microscopic image contrast. In B, the presence of carminic acid granules in the cytoplasm is more evident.

C are younger undifferentiated chromatocytes that once mature will begin to increase their production of carminic acid.

FIG. 2 shows the results of the Percoll® (polyvinylpyrrolidone-coated silica particle) gradient (separation phases) and carbamate formation (cellular product) on the surface of the last two tubes as a black supernatant.

Figure 3:
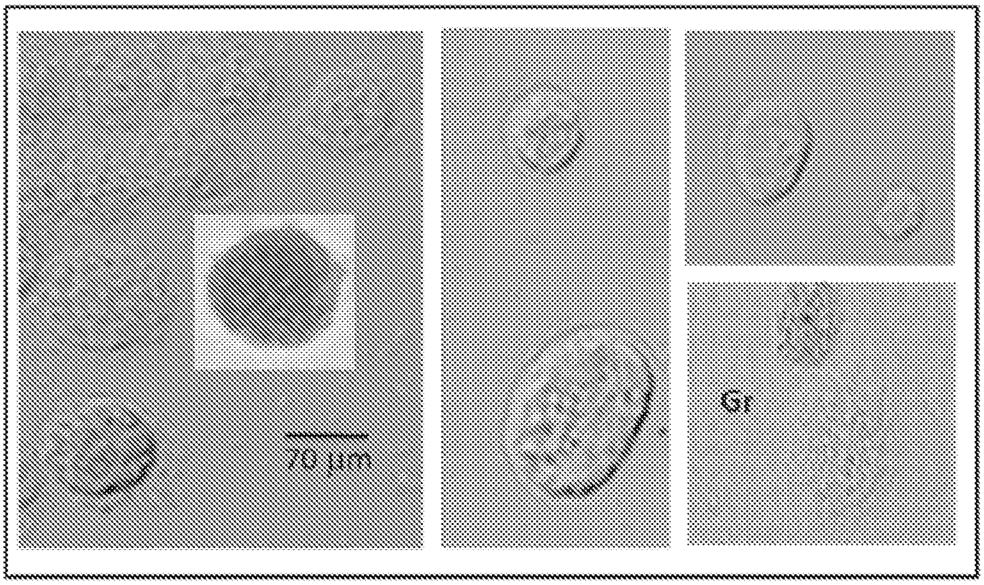

FIG. 3 shows a phase contrast microscopy of mitogen-stimulated hemocytes after 72 hours cultured in Schneider culture medium.

Figure 4:
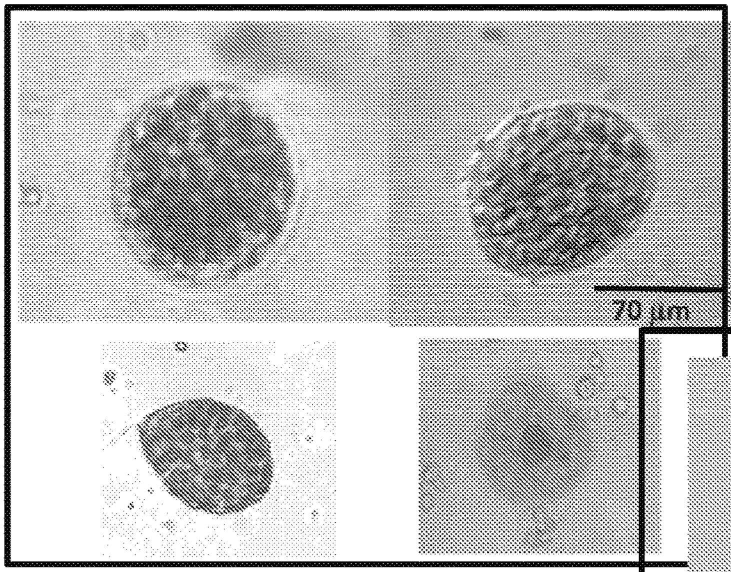

FIG. 4 shows a bioproduction microscopy of cell viability in Schneider medium culture 72 hours after inoculation, 2 Mm plate culture MTT assay.

Figure 5:
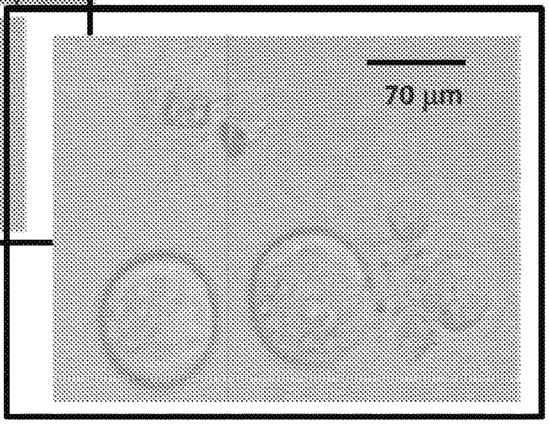

FIG. 5 shows a microscopy of the granulocytes 96 hours after inoculation.

Figure 6:
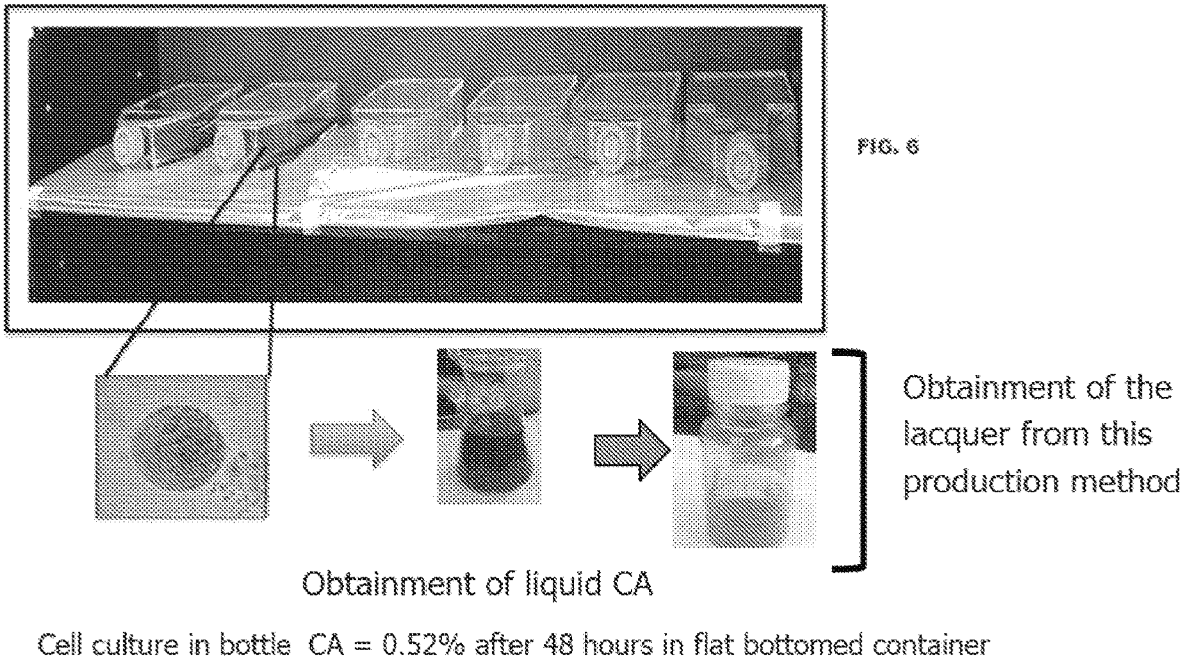

FIG. 6 shows a representation of the production and maintenance process in flat-bottomed containers according to one embodiment of the invention.

Figure 7:
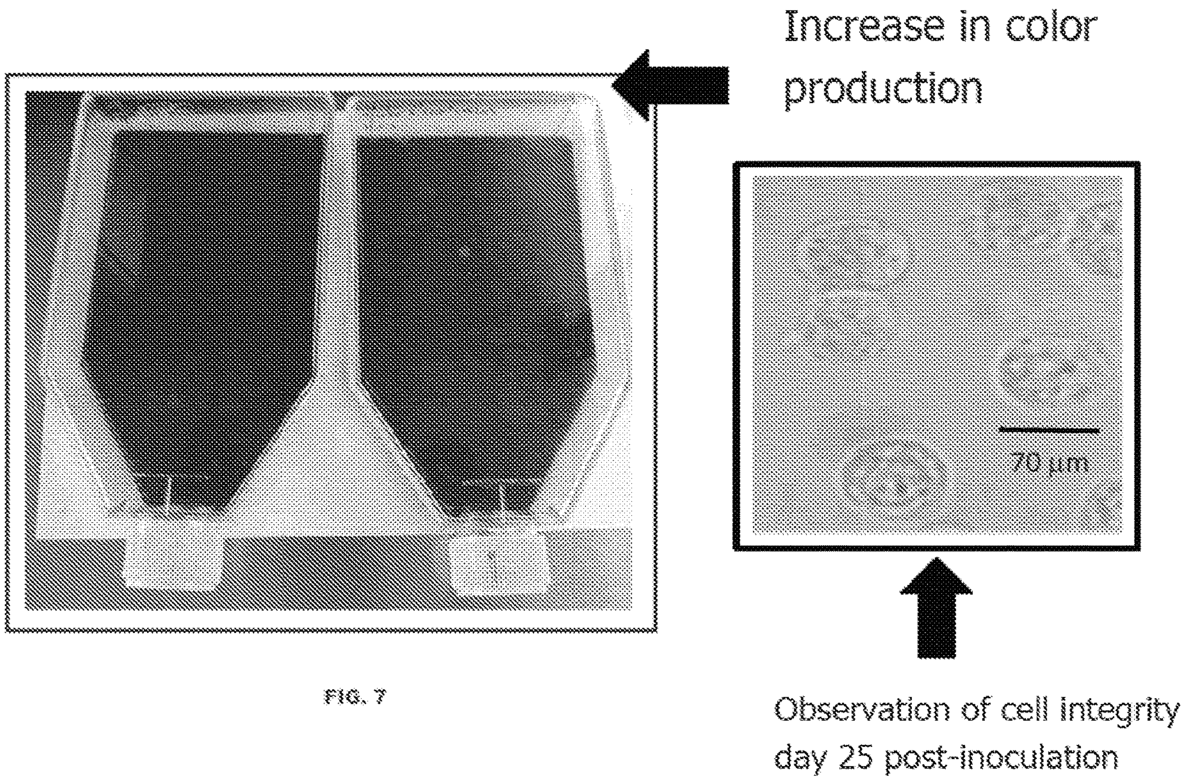

FIG. 7 shows the results of the inspection in containers on day 25 post inoculation.

Figure 8:
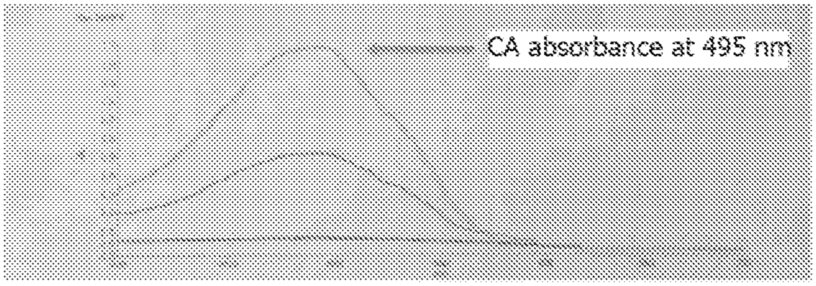

FIG. 8 shows a graph of results that describes the absorption spectrum (absorbance vs. wavelength in nanometers) for the identification of CA in bioculture from the table of example 1 detailed in the examples section below.

Figure 9:
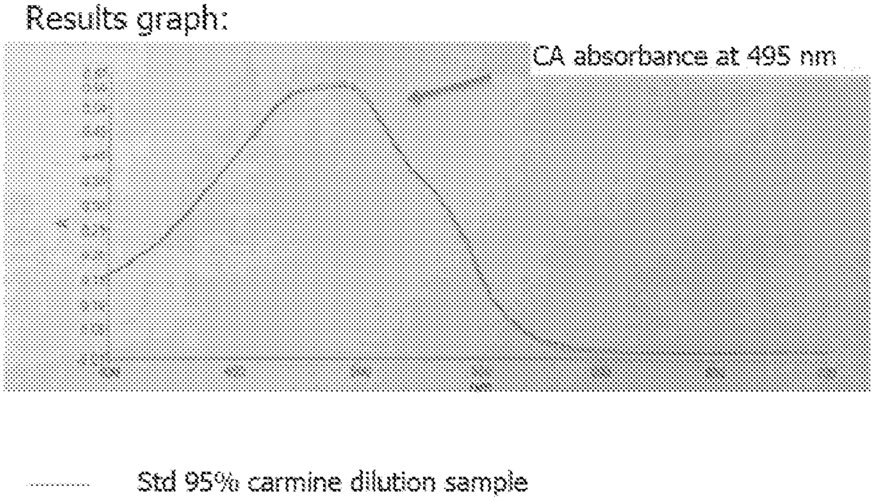

FIG. 9 shows a graph of results that describes the absorption spectrum for the identification of CA in purified bioculture from the table of example 2 detailed in the examples section below.

Figure 10:
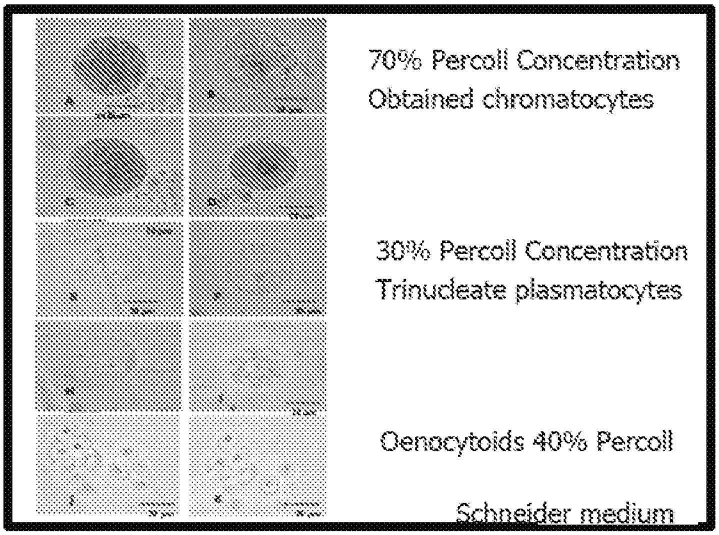

FIG. 10 complementary to table 2 described below, said figure shows preliminary results of the different cell types obtained by Percoll® (polyvinylpyrrolidone-coated silica particle) gradient (microscopy of cells obtained in Percoll® (polyvinylpyrrolidone-coated silica particle) gradient) of the method detailed below.

Figure 11:
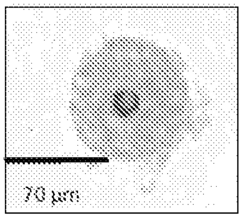

FIG. 11 shows a micrograph of a cultured granulocyte on day 8.

Figure 12:
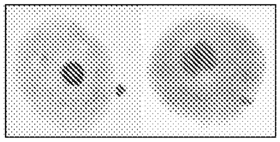

FIG. 12 shows a micrograph of a cultured granulocyte on day 10.

Figure 13:
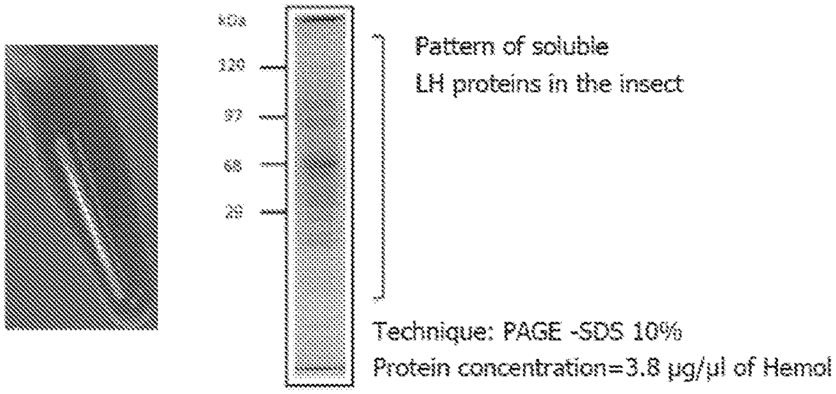

FIG. 13 shows an anticoagulant effect in obtaining hemolymph by perfusion.

Figure 14:
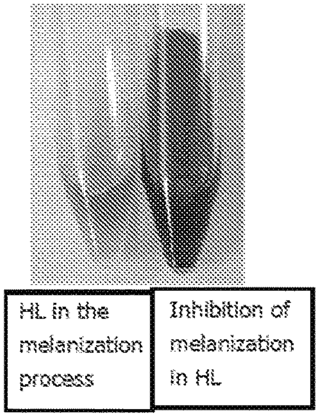

FIG. 14 shows the integrity of the proteins obtained during the perfusion.

DETAILED DESCRIPTION OF THE INVENTION

The following definitions are provided to allow a better understanding of the invention:

The use of the term "approximate/approximately" provides a certain additional range. The term is defined as follows. The additional range provided by the term is approximately ±10%. By way of non-limiting example, if it says "approximately 40 grams", the range is between ±10% of standard deviation and so on for the other measurements.

According to the present invention, the in vitro production of carminic acid comprises: extracting, isolating, purifying and maintaining a hemocyte cell line obtained from egg-filled adult females of the *Dactylopius coccus* Costa cochineal scale insect in the following general manner:

Extraction of Hemocytes from the Hemolymph:

Hemolymph is obtained by perfusion of the hemocele of egg-filled pregnant strains of *Dactylopius coccus* using an anticoagulant buffer solution comprising a base, an ionic salt, a chelating agent and an organic acid until a red pigmented solution containing cells that produce carminic acid (CA) among others is obtained.

In one embodiment of the invention, the anticoagulant buffer comprises NaOH, NaCl, EDTA and citric acid.

The pigmented solution obtained is deposited in sterile containers and centrifuged.

The supernatant is recovered.

On the other hand, a discontinuous Percoll® (polyvinylpyrrolidone-coated silica particle) gradient is prepared with phosphate-buffered saline.

The discontinuous Percoll® (polyvinylpyrrolidone-coated silica particle) gradient is pre-run by centrifugation.

Once the pre-run is finished, the pigmented solution obtained is added.

It is run by centrifugation to obtain identified cells (Table 2).

At the end of the run, the hemolymph cells that will be used to generate a culture are obtained.

The cells are recovered and plated with growth medium for culturing insect cell lines for adaptation.

Selection of the Cell Line and Obtaining Primary Cultures:

Cultures that show differentiated cells under the microscope are reviewed, evaluated, and selected.

Granulocytes and hemocytes are selected.

The selected cells are plated with growth medium for culturing insect cell lines for adaptation.

Finally, they are reviewed and evaluated according to their phenotype cell integrity.

Stimulation and Activation of Cell Lines:

A combination of mitogens in phosphate-buffer saline is added to each cultured cell to promote mitosis.

The cultures are incubated until they gradually turn red and cells are observed in cell division due to the mitogens.

Cultures that show an increase in their population density are selected and propagated in a container in which it is recommended to prepare a cryogenic preserve.

Propagation and Production in Container:

The selected cells are plated with growth medium for culturing insect cell lines for adaptation.

The containers are incubated for approximately 10-14 days (primary line). During this time, the cells form a confluent monolayer of cells attached to the containers, and the culture medium turns red as a positive sign of color production.

The containers are checked every day to assess and check for the presence of mitosis.

At the end of the cycle, the cultures are harvested and the color is milked or harvested from each of the culture containers.

The "milking" or "harvest" is done in a disinfected environment and each harvest is centrifuged in containers with the purpose of eliminating cell debris and only recovering the supernatant, which in this case is: "The pigment" (carminic acid).

For the purposes of the present invention, the steps of the above-mentioned method are presented in detail:

Extraction of Hemocytes from the Hemolymph:

First of all, from at least approximately 20 to approximately 95 mg of egg-filled pregnant strains of *Dactylopius coccus*, preferably from approximately 30 to approximately 85 mg of egg-filled pregnant strains of the insect, hemolymph is obtained by perfusion of the hemocele of the strain with an anticoagulant buffer reported in the literature by Graham et al., 1986 composed of a range of approximately 0.25 mM to approximately 0.75 mM NaOH, preferably approximately 0.61 mM; a range of approximately 0.15 M to approximately 0.50 M NaCl, preferably approximately 0.56 M; a range of approximately 0.10 mM to approximately 0.25 mM EDTA, preferably approximately 0.16 mM; a range of approximately 100 mM to approximately 250 mM citric acid, preferably approximately 100 mM; at an approximate pH in the range of 4.5-6.5 as can be seen in table 1 below. The solution obtained is a red pigmented solution in which the cells that produce carminic acid (CA) are suspended, as well as other cellular variants (hemocytes) of the hemolymph.

The pigmented solution obtained is deposited in sterile containers, preferably for the purposes of the present invention in sterile polypropylene conical tubes, and is centrifuged at a range of approximately 500-1200 revolutions per minute (rpm), preferably approximately 600-1000 rpm, for approximately 8-17 minutes, preferably approximately 10-15 minutes at a temperature in the range of approximately 2-5° C., preferably approximately 4° C.

The supernatant is recovered in sterile containers, preferably for the purposes of the present invention in sterile polypropylene conical tubes, and kept at room temperature.

Additionally, a discontinuous Percoll® (polyvinylpyrrolidone-coated silica particle) gradient (approximately 10-90% range, preferably approximately 20-80% range) is prepared with phosphate-buffered saline (1×PBS at a pH range of approximately 4.5 to 5.2, preferably at a pH of approximately 5.5) as can be seen in table 2 below and in FIG. 10 in the figures section.

TABLE 1

Percoll ® (polyvinylpyrrolidone-coated silica particle) gradients used

| Gradient (Concentration) | Centrifuge Speed | Cells Identified |
|---|---|---|
| Percoll ® 90% | 1500 rpm/5 min | Trinucleated plasmatocytes, Mature granulocytes. |
| Percoll ® 70% | 1000 rpm/5 min | Abundant granulocytes. |
| Percoll ® 50% | 1000 rpm/10 min | Few granulocytes, abundant oenocytoids. |
| Percoll ® 40% | 700 rpm/10 min | Few granulocytes, abundant oenocytoids |
| Percoll ® 40% | 1000 rpm/10 min | Few granulocytes, abundant oenocytoids |
| Percoll ® 40% | 800 rpm/10 min | Few granulocytes, abundant oenocytoids |
| Percoll ® 30% | 1000 rpm/10 min | Abundant trinucleated plasmatocytes. Few granulocytes. |
| Percoll ® 40% | 600 rpm/5 min | Abundant mature and young granulocytes. |

The gradient is pre-run by centrifuging at a range of at least approximately 4000-5500 rpm, preferably at a range of approximately 4500-5000 rpm, during approximately 12-22 minutes, preferably approximately 15 to 20 minutes.

After the end of the pre-run, an amount in a range of approximately 95-550 μl is added, preferably in a range of approximately 100-500 μl, of the pigmented solution obtained.

Centrifuge at approximately 1000 revolutions per minute (rpm) for from approximately 10 to approximately 20 minutes, preferably approximately 15 minutes, at room temperature, to obtain the following results as can be seen from table 2, which is reproduced again below and in FIG. 10 in the figures section.

TABLE 2

Percoll ® (polyvinylpyrrolidone-coated silica particle) gradients used

| Gradient (Concentration) | Centrifuge Speed | Cells Identified |
|---|---|---|
| Percoll ® 90% | 1500 rpm/5 min | Trinucleated plasmatocytes, Mature granulocytes. |
| Percoll ® 70% | 1000 rpm/5 min | Abundant granulocytes. |
| Percoll ® 50% | 1000 rpm/10 min | Few granulocytes, abundant oenocytoids. |
| Percoll ® 40% | 700 rpm/10 min | Few granulocytes, abundant oenocytoids |
| Percoll ® 40% | 1000 rpm/10 min | Few granulocytes, abundant oenocytoids |
| Percoll ® 40% | 800 rpm/10 min | Few granulocytes, abundant oenocytoids |
| Percoll ® 30% | 1000 rpm/10 min | Abundant trinucleated plasmatocytes. Few granulocytes. |
| Percoll ® 40% | 600 rpm/5 min | Abundant mature and young granulocytes. |

At the end of the centrifugation run, several phases are obtained, the interface between the Percoll® (polyvinylpyrrolidone-coated silica particle) and the dye (pigment) contains the purified hemolymph cells that will be used to generate a primary culture (phase I).

Cells are recovered and plated, preferably but in a non-limiting manner, in 16-well multi-well plates with approximately 100 μl to approximately 500 μl, preferably approximately 250 μl, of culture medium for culturing insect cell lines, preferably commercial Schneider medium, for approximately 20-30 hours, preferably for approximately 24-26 hours at an approximate temperature in a range of approximately 20-28° C., preferably at a range of approximately 22-26° C. for adaptation.

Selection of the Cell Line and Obtaining Primary Cultures:

Approximately 24 hours after culture, the cultures that show better cell integrity and phenotype under the microscope are reviewed, evaluated, and selected.

The following cell variants are selected: "Young granulocytes" and "young undifferentiated hemocytes" (SELECTION OF CANDIDATES).

These two variants are selected and replated into plates, preferably but in a non-limiting manner, into 16-well multiwell plates with approximately 100 μl to approximately 500 μl, preferably approximately 250 μl, of culture medium for culturing insect cell lines, preferably commercial Schneider medium, for approximately 20-30 hours, preferably approximately 22-26 hours at a temperature in a range of approximately 20-28° C., preferably in a range of approximately 22-26° C. for adaptation.

Finally, approximately 24 hours later they are reviewed and evaluated according to their cellular integrity and maintenance of the phenotype.

Stimulation and Activation of Cell Lines:

To each of the wells containing cells in culture is added a combination of mitogens (concanavalin A at a range of approximately 0.20-0.30 micromoles, preferably approximately 0.25 micromoles+phytohemagglutinin at a range of approximately 0.40-0.60 micromoles, preferably approximately 0.50 micromoles) in phosphate-buffered saline (1×PBS at a pH between approximately 4.8-5.2, preferably approximately pH 5.0), to promote mitosis in the young granulocytes.

Cultures are incubated at a temperature range of approximately 20-28° C., preferably at a range of approximately 22-26° C. for approximately 20-50 hours, preferably approximately 24-48 hours, where they gradually turn red and cells are observed in cell division due to the mitogens.

Cultures that show an increase in population density are selected and taken to the stage of propagation and production in containers.

In the container propagation stage, it is recommended to prepare a cryogenic preserve for storage in liquid nitrogen tanks (in a range between approximately −160 to −180° C., preferably at approximately −170° C.) for approximately two to three months.

Propagation and Production in Container:

Plated cells are cultured in containers with culture medium for the growth of insect cell lines. For the purposes of the present invention, flat-bottomed containers with a surface area in the range of approximately 200-300 $cm^2$ are preferred, more preferably containers with a surface area of approximately 225 cm2; for this, by way of example, approximately 200 μl of the plate culture is used and inoculated in a range of approximately 200-350 μl, more preferably in a range of approximately 250-300 μl of culture medium for culturing cell lines of insects, preferably Schneider culture medium.

The containers are incubated at a range of approximately 20-28° C., preferably at a range of approximately 22-26° C. for approximately 10-14 days, preferably for approximately 12-13 days (primary line). During this time period, the cells form a confluent monolayer of cells attached to the containers, and the culture medium turns red as a positive sign of color production.

The containers are checked approximately every 24 hours to assess and check for the presence of mitosis in the cell lines.

At the end of the cycle, the cultures are harvested and the color is milked or harvested from each of the culture containers.

The "milking" or "harvest" is performed in a sanitized environment and each harvest is centrifuged in containers. For the purposes of the present invention, conical tubes with a capacity of approximately 40-60 ml in volume are preferred, more preferably a capacity of approximately 50 ml, at a speed range of approximately 3500-5500 rpm, preferably 4000-5000 rpm for approximately 18-22 minutes, preferably approximately 20 minutes, for the purpose of removing cellular debris and only recovering the supernatant, which is in this case: "The pigment" (carminic acid).

It is important to mention that the prior art discloses that with conventional methods of carminic acid production, thousands of insects are required to produce approximately 1 kg of carminic acid (CA). In addition, a high-quality host plant is required, which in these cases is the Opuntia ficus-indica cactus plant, which must be constantly replaced or cultivated (costs) as well as a preventive and prophylactic phytosanitary control of the stalk that implies the use of human resources for the constant care of the culture; for harvests, growth cycles of 80-90 days are required for the insect to grow, reach adulthood and be harvested; In addition, for the production of CA, a drying process is required after the harvest, in which there are natural production losses. Approximately in a 3:1 ratio (live insect:dry insect), there is a presence of pests and predators that reduce production at times, there are high production costs due to all of the above, the international price is monopolized by countries that produce high quantities of CA, the price is set arbitrarily because it is the only form of production and because in countries with high production the biogeographical conditions allow large quantities to be produced per year, so large production areas are required to produce attractive quantities of CA.

In some embodiments of the present invention, the propagation and production of carminic acid in containers may be performed in containers such as, but not limited to, flat bottom culture bottles, Roux Flasks, benchtop bioreactors, specialized bioreactors, industrial bioreactors, containers in which a chemical process is carried out that involves organisms, microorganisms or biochemically active substances derived from said organisms and/or microorganisms and/or any other suitable container or device where a propagation reaction can be carried out such as the one described in the present invention.

EXAMPLES

Example 1.—Absorption Spectrum for Identification of CA in Bioculture

Results table:

| Sample ID | Description | CA Absorbance 494 nm | % CA |
|---|---|---|---|
| Std 95% carmine sample | 0.1 g | 1.088 | 1.521 |
| Sample carmine batch 1 | Previous rack batch | 0.0703 | 0.09823 |
| Sample carmine batch 2 | 0.1 g | 0.5208 | 0.7277 |

Filtration was performed with a PVOF membrane (0.2 mm)/heating for 30 minutes (55° C.).

Example of obtaining the % of CA with result 3:

Formula: % CA=0.5208/0.139×0.1 g=37.46%

Example 2.—Absorption Spectrum for the Identification of CA in Purified Bioculture Results table:

| Sample ID | Description | CA absorbance 494 nm | % CA |
|---|---|---|---|
| Std 95% carmine sample | 0.05 g | 0.5562 | 0.7772 |

Example of obtaining the % of CA:

Formula: % CA=0.5562/0.139×0.05 g=80.02%

Although the foregoing embodiments of the invention have been described in some detail by way of illustration and example for the purpose of improving their understanding, the descriptions and examples are not to be construed as limiting the scope of the invention, but only to illustrate some of the variations that are comprised within the spirit and scope thereof. As will be evident to a person with average knowledge in the matter, variations or modifications that do not depart from the spirit of the invention are within its scope. Descriptions of the scientific literature cited herein are expressly incorporated by reference.

What is claimed is:

1. A method for the production of carminic acid from female insects of the species *Dactylopius coccus*, the method comprising:

extracting hemocytes from the hemolymph of the female insects until obtaining a solution comprising carminic acid-producing cells;

pre-running a polyvinylpyrrolidone-coated silica particle gradient solution;

adding the solution comprising the carminic acid-producing cells to the pre-run polyvinylpyrrolidone-coated silica particle gradient solution to obtain a mixture comprising hemocytes;

purifying the hemocytes from the mixture;

recovering the purified hemocytes;

culturing the purified hemocytes with culture medium for culturing insect cell lines;

stimulating and activating the insect cell lines; and propagating the insect cell lines that produce carminic acid;

wherein stimulating and activating the insect cell lines comprises adding a combination of mitogens in phosphate-buffered saline, incubating the insect cell lines with the combination of mitogens to generate cultures, and after incubation, selecting the cultures that show an increase in population density; and wherein the hemocytes are granulocytes.

2. The method according to claim 1, wherein extracting hemocytes from the hemolymph of the female insects is performed by perfusion of the hemocele with an anticoagulant buffer solution comprising a base, an ionic salt, a chelating agent and an organic acid;

wherein the polyvinylpyrrolidone-coated silica particle gradient solution is prepared with a phosphate-buffered saline solution;

wherein the step of pre-running the polyvinylpyrrolidone-coated silica particle gradient is performed by centrifugation; and, wherein the step of purifying the hemocytes from the mixture is performed by centrifugation.

3. The method according to claim 1, wherein prior to stimulating and activating the cell lines, the method comprises selecting young granulocytes and culturing the selected cells with culture medium for culturing insect cell lines.

4. The method according to claim 1, wherein propagating the insect cell lines that produce carminic acid comprises:

selecting cells from the cultures that show an increase in population density;

culturing the selected cells in containers with culture medium for the growth of insect cell lines; and harvesting the cultures and harvesting the carminic acid (color) produced.

5. The method according to claim 1, wherein the polyvinylpyrrolidone-coated silica particle gradient is approximately 10-90%.

6. The method according to claim 1, wherein the cultures are incubated for approximately 20-50 hours at a temperature in the range of approximately 20-28° C.

7. The method according to claim 1, wherein the cultures that show an increase in population density are preserved in a cryogenic phase with liquid nitrogen.

8. The method according to claim 7, wherein the cryogenic phase is carried out at a temperature in an approximate range between −160° C. to −180° C. for approximately 2-3 months.

9. The method according to claim 1, wherein the step of extracting hemocytes from the hemolymph of the female insects comprises providing approximately 20 mg to approximately 95 mg of egg-filled pregnant drains of the insect *Dactylopius coccus*.

10. The method according to claim 2, wherein the anticoagulant buffer comprises from 0.25 mM to approximately 0.75 mM NaOH; a range of approximately 0.15 M to approximately 0.50 M NaCl; a range of approximately 0.10 mM to approximately 0.25 mM EDTA; a range of approximately 100 mM to approximately 250 mM citric acid; at an approximate pH in the range of 4.5-6.5.

11. The method according to claim 10, wherein the anticoagulant buffer comprises 0.61 mM NaOH; 0.56 M NaCl; 0.16 mM EDTA; 100 mM citric acid; at an approximate pH in the range of 4.5-6.5.

12. The method according to claim 3, wherein the insect cell line culture medium is Schneider culture medium.

13. The method according to claim 4, wherein the mitogens are concanavalin A at a range of approximately 0.20-0.30 micromoles with phytohemagglutinin at a range of approximately 0.40-0.60 micromoles.

* * * * *